US009849228B2

(12) United States Patent
Noack et al.

(10) Patent No.: US 9,849,228 B2
(45) Date of Patent: Dec. 26, 2017

(54) METHOD FOR DETERMINING AT LEAST ONE PARAMETER OF AN EXTRACORPOREAL BLOOD CIRCUIT AS WELL AS APPARATUSES

(75) Inventors: Joachim Noack, Bad Neustadt (DE); Wei Zhang, Niederwerrn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1144 days.

(21) Appl. No.: 13/545,403

(22) Filed: Jul. 10, 2012

(65) Prior Publication Data

US 2013/0025357 A1 Jan. 31, 2013

Related U.S. Application Data

(60) Provisional application No. 61/513,005, filed on Jul. 29, 2011.

(30) Foreign Application Priority Data

Jul. 29, 2011 (DE) ......................... 10 2011 108 786

(51) Int. Cl.
*G01F 17/00* (2006.01)
*F17D 3/00* (2006.01)
*A61M 1/36* (2006.01)

(52) U.S. Cl.
CPC ........ *A61M 1/3643* (2013.01); *A61M 1/3644* (2014.02); *A61M 2205/3306* (2013.01);
(Continued)

(58) Field of Classification Search
CPC .............. A61M 1/3643; A61M 1/3647; A61M 1/3644; A61M 1/3646; A61M 1/3649;
(Continued)

(56) References Cited

U.S. PATENT DOCUMENTS 4,372,846 A * 2/1983 Yamagami .......... A61M 1/3441
210/321.65
5,855,201 A 1/1999 Fukui et al.
(Continued)

FOREIGN PATENT DOCUMENTS

CN  101193670      6/2008
CN  101678161 A    3/2010
(Continued)

OTHER PUBLICATIONS

Japanese Search Report by Registered Searching Organization in Japanese Application No. 2014-521973, dated Apr. 6, 2016, 9 pages (with English translation).

*Primary Examiner* — Daniel S Larkin
(74) *Attorney, Agent, or Firm* — Fish & Richardson P.C.

(57) ABSTRACT

A method for determining at least one parameter of an extracorporeal blood circuit includes the steps of filling an extracorporeal blood circuit, e.g., encompassing a medical functional device, a treatment device and/or a blood tube set, by introducing a fluid, and detecting a volume of the introduced fluid which is required for filling the extracorporeal blood circuit by a detection device. A control device, a treatment apparatus, a computer readable storage medium, a computer program product as well as a computer program are also described.

26 Claims, 3 Drawing Sheets

(52) U.S. Cl.
CPC ............... *A61M 2205/3368* (2013.01); *A61M 2205/3375* (2013.01); *A61M 2205/3379* (2013.01); *A61M 2205/3393* (2013.01); *Y10T 137/0318* (2015.04)

(58) Field of Classification Search
CPC .............. A61M 1/3652; A61M 1/3621; A61M 1/3624; A61M 1/3626; A61M 1/3663; A61M 1/3664; G06F 19/3481
See application file for complete search history.

(56) References Cited

U.S. PATENT DOCUMENTS

| | | | |
|---|---|---|---|
| 6,270,673 | B1 | 8/2001 | Belt et al. |
| 7,947,180 | B2 | 5/2011 | Apel et al. |
| 9,119,922 | B2* | 9/2015 | Nuernberger ......... A61M 1/342 |
| 2008/0237128 | A1* | 10/2008 | Rovatti ............... A61M 1/3643 210/646 |
| 2009/0101550 | A1* | 4/2009 | Muller .................... A61M 1/16 210/87 |
| 2009/0230036 | A1 | 9/2009 | Apel et al. |
| 2010/0192686 | A1 | 8/2010 | Kamen et al. |
| 2011/0168291 | A1 | 7/2011 | Beden et al. |
| 2012/0024080 | A1* | 2/2012 | Carbone, II .............. G01F 3/10 73/861.04 |

FOREIGN PATENT DOCUMENTS

| | | |
|---|---|---|
| DE | 10 2008 045 422 A1 | 3/2010 |
| DE | 102009024468 A1 | 12/2010 |
| EP | 1 924 304 B1 | 1/2011 |
| JP | S54103397 | 8/1979 |
| JP | 03-277372 A | 12/1991 |
| JP | H09218887 | 8/1997 |
| JP | H09290020 | 11/1997 |
| JP | 3947037 B2 | 7/2007 |
| JP | 2008540003 | 11/2008 |
| JP | 4313264 B2 | 8/2009 |
| JP | 2009-297339 A | 12/2009 |
| JP | 2011509803 | 3/2011 |
| WO | WO/2010/133319 * | 11/2010 |

* cited by examiner

METHOD FOR DETERMINING AT LEAST ONE PARAMETER OF AN EXTRACORPOREAL BLOOD CIRCUIT AS WELL AS APPARATUSES

CROSS-REFERENCE TO RELATED APPLICATIONS

The present application claims priority to U.S. Provisional Application No. 61/513,005, filed on Jul. 29, 2011, and claims priority to Application No. DE 10 2011 108 786.2, filed in the Federal Republic of Germany on Jul. 29, 2011, each of which is expressly incorporated herein in its entirety by reference thereto.

FIELD OF INVENTION

The present invention relates to a method for determining at least one parameter of an extracorporeal blood circuit. It further relates to a control device as well as a treatment apparatus. Furthermore, the present invention relates to a digital storage medium, a computer program product as well as a computer program.

BACKGROUND INFORMATION

In practice, extracorporeal blood circuits undergo preparation prior to being used in a medical treatment method. The treatment apparatus utilized for the treatment with the extracorporeal circuit is in practice adapted to the upcoming treatment modality and/or to the utilized (disposable) articles such as blood circuit or blood filter before the beginning of the treatment. For this purpose, the extracorporeal blood circuit is usually filled with a fluid (for example, a substituate solution) before its use and flushed herewith in order to remove possibly present production residues and/or air bubbles from the extracorporeal blood circuit; Occasionally, the treatment apparatus is set at a defined treatment modality at which it should or may be used for the treatment, or which type or which size the utilized blood filter or blood circuit is. It is necessary to know at least one parameter both for determining a minimum flush volume for the blood circuit and for adapting the treatment apparatus to the utilized (disposable) articles.

SUMMARY

An object of the present invention is to specify a method for, preferably automatically, determining at least one parameter of an extracorporeal blood circuit.

Furthermore, a control device which is provided for executing the method according to the present invention, a treatment apparatus by means of which the method according to the present invention is executable as well as a suitable digital storage medium, a suitable computer program product and a suitable computer program are to be specified.

An object according to the present invention is accomplished by means of a method described herein. In addition, it is accomplished by means of a control device as well as a treatment apparatus. An object according to the present invention is further accomplished by means of a digital storage medium, a computer program product as well as computer program.

All advantages that are achievable by means of the method according to the present invention may in certain embodiments according to the present invention undiminishedly also be achieved by means of the apparatuses according to the present invention.

The method according to the present invention is suitable and provided for determining at least one parameter of an extracorporeal blood circuit.

The method according to the present invention encompasses filling the extracorporeal blood circuit by introducing a medical fluid.

It further encompasses detecting or determining the size or value of a volume or an amount of the introduced fluid which is required for filling the extracorporeal blood circuit or for filling a certain section hereof (for example up to a detector section or up to a recognition device such as an air detector).

Detecting or determining the volume or the amount takes place by means of a device, in particular automatically.

The control device according to the present invention, which can also be a detection device or be used as such, is suitable and provided, designed and/or configured for executing the method according to the present invention.

The treatment apparatus according to the present invention is provided and embodied, equipped and/or configured for executing the method according to the present invention and/or for its automated adjusting based on the results of the method according to the present invention.

Thereby, all or some of the mechanically executed steps of the method according to the present invention may be performed.

A computer program product according to the present invention comprises a program code saved on a machine-readable medium for executing the mechanical steps of the method according to the present invention when the computer program product runs on a computer.

The term "machine-readable medium" denotes in certain embodiments of the present invention a medium containing data or information which is interpretable by software and/or hardware. The medium may be a data medium like a disk, a CD, DVD, a USB stick, a flashcard, an SD card or the like.

A computer program according to the present invention comprises a program code for executing the mechanical steps of a method according to the present invention when the computer program runs on a computer.

It also applies to the computer program product according to the present invention and the computer program according to the present invention that all or some of the mechanically executed steps of the method according to the present invention are performed.

A digital, particularly a non-volatile storage medium according to the present invention, particularly in the form of a machine-readable data storage device, particularly in the form of a disk, CD, DVD or EPROM, particularly with electronically or optically readable control signals, may interact with a programmable computer system such that the mechanical steps of a method according to the present invention are performed.

Hereby, all, several or some of the mechanically executed steps of the method according to the present invention may be performed.

A computer program product according to the present invention comprises a program code stored on a machine-readable data storage device for executing the mechanical steps of the method according to the present invention when the computer program product runs on a computer. According to the present invention a computer program product can be understood as, for example, a computer program which is stored on a storage device, an embedded system as a comprehensive system with a computer program (e.g. an electronic device with a computer program), a network of computer-implemented computer programs (e.g. a client-server system, a cloud computing system, etc.), or a computer on which a computer product is loaded, executed, saved or developed.

A machine-readable data storage device denotes in certain embodiments of the present invention a medium that contains data or information which is interpretable by software and/or hardware. The medium may be a disk, a CD, DVD, a USB stick, a flash card, an SD card or the like.

A computer program according to the present invention comprises a program code for executing the mechanical steps of a method according to the present invention when the computer program runs on a computer. A computer program according to the present invention can be understood as, for example, a physical software product, which is ready for distribution and contains a computer program.

Embodiments according to the present invention may comprise some or all of the following features in various combinations.

In all of the following embodiments, the use of the expression "may be" or "may have" and so on, is to be understood synonymously with "preferably is" or "preferably has," respectively, and so on, and is intended to illustrate exemplary embodiments according to the present invention.

An extracorporeal blood circuit comprises in certain embodiments of the present invention a medical functional device. This functional device may for example comprise or be a blood cassette (in particular embodied as disposable), and/or a treatment device, such as for example a dialyzer or a blood filter, and/or a blood tube set.

The size of the volume (in short also: the volume) is in some embodiments according to the present invention a numerical value with a dimension (such as milliliters (ml)) or without dimension. In other embodiments according to the present invention, a classification of the volume or its allocation to certain volume grades is understood.

"Filling" denotes in certain embodiments of the present invention introducing or filling in—in particular medical—fluid, e.g., substituate liquid and/or dialyzing liquid, into the extracorporeal blood circuit. In some embodiments according to the present invention, filling takes place once and/or initially, i.e. before the beginning of the treatment of the patient, for example a blood treatment method, e.g., a dialysis (hemodialysis, hemofiltration, hemodiafiltration or the like) and/or before the beginning of the flushing process.

In certain embodiments of the present invention, filling in the sense of the present invention was started, has taken place or was completed before the flushing process.

The extracorporeal blood circuit is in some embodiments according to the present invention completely or basically completely filled with fluid when being filled.

In doing so, in some embodiments according to the present invention, so much fluid is introduced into the extracorporeal blood circuit, that the introduced volume corresponds to an inner volume or a maximum (intake) volume of the extracorporeal blood circuit (with or without components which are in fluid connection herewith, such as a blood filter or a blood cassette).

In order to record the volume of the extracorporeal blood circuit or a section hereof, the extracorporeal blood circuit does not have to be completely filled with fluid in some embodiments according to the present invention.

Thus, in certain embodiments according to the present invention, the extracorporeal blood circuit is for example only filled with fluid partially, e.g., up to a certain point, for example a recognition device which is arranged in or at the extracorporeal blood circuit, used for recognizing a fluid or for recognizing a change between different fluids.

In some embodiments, it may for example be provided to round up or estimate the (filling) volume or whole volume or whole inner volume or capacity of the extracorporeal blood circuit. This projection or estimation is based on the size of the detected volume (this is, for example, the filled section of the extracorporeal blood circuit between the introduction point of the fluid and the recognition point) and on the knowledge of the remaining part of the whole extracorporeal blood circuit.

The fluid which was introduced into the extracorporeal blood circuit is in some embodiments according to the present invention a priming liquid and/or a flushing liquid, for example a substituate liquid.

In certain embodiments, the method according to the present invention encompasses processing the detected size of the volume of the fluid. Processing serves in some embodiments according to the present invention to maintain the at least one parameter or in the most general sense a specification.

Processing the detected size is or encompasses in some embodiments according to the present invention making a statement about the parameter.

Processing the detected size of the volume is or encompasses in some embodiments according to the present invention converting the value of the volume via algorithms, functions or coherencies to maintain the parameter. They may be or get stored in a storage device, for example in a storage or control device of a treatment apparatus.

Processing the detected size of the volume is or encompasses in some embodiments according to the present invention communicating the received parameter to a supervisor; in other embodiments, however, it does not.

Processing the detected size of the volume is or encompasses in certain embodiments according to the present invention comparing the detected volume with sizes or specifications which are suitable for detecting the parameter (for example, by means of a comparative table).

Processing the detected size of the volume is or encompasses in certain embodiments according to the present invention allocating a parameter to the extracorporeal blood circuit and/or to individual components hereof based on the detected size of the volume.

Processing the detected size of the volume encompasses in some embodiments according to the present invention communicating the parameter to a supervisor (for example, by means of a display indication, error message, alarm or the like); in other embodiments, however, it does not.

A parameter is in some embodiments according to the present invention a specification which is typical for the utilized extracorporeal blood circuit. These include specifications which describe the extracorporeal blood circuit, make it distinctive, indicate its size, its type, its suitability for certain treatment modalities or treatment methods or its suitability for its use with certain treatment apparatuses, make statements on individual components hereof (e.g., present or not present), and the like.

A parameter, in terms of the present invention, may be a parameter value, a characteristic or a size of a parameter, a numerical value with dimension, a numerical value without dimension, a type, a classification and the like.

In some embodiments of the present invention a parameter is a specification which is typical or characteristic for the extracorporeal blood circuit used. It can be exclusive (the specification or the parameter is unambiguously assigned only to the type of extracorporeal blood circuits used) or not exclusive (the specification or the parameter is not only assigned to the extracorporeal blood circuit used or the type of extracorporeal blood circuits used but also to other blood circuits or types of blood circuits. The specification or parameter allows though a certain allocation, e.g. to a selected group of extracorporeal blood circuits).

The volume of the fluid which is introduced into the extracorporeal blood circuit for its filling is, in certain embodiments according to the present invention, a cumulative volume.

A cumulative volume denotes in certain embodiments of the present invention the whole volume of fluid which was introduced into the extracorporeal blood circuit initially or once, in particular completely or substantially completely filling the extracorporeal blood circuit. The cumulative volume thus also encompasses partial volumes which have to be replaced or refilled in order to achieve initial filling of the extracorporeal blood circuit, e.g., due to ventilation of the extracorporeal blood circuit which takes place during and due to filling, to achieve the desired amount.

Reaching the filled state of the extracorporeal blood circuit is determined by means of a recognition device for recognizing a fluid or a fluid condition (such as a coloration, a mixing ratio, an exchange of different fluids, for example, a displacement of air by means of the fluid, a transition area between a liquid fluid and air, and so on).

The recognition device is in certain embodiments of the present invention arranged in or at the extracorporeal blood circuit. In some embodiments according to the present invention, it is in operative or signal connection with it.

In certain embodiments of the present invention, the recognition device is chosen from level detectors (for example ultrasound level detectors, capacitive level detectors, optical level detectors or the like), air detectors (for example air bubble detectors), venous bubble traps, or the like, or combinations hereof which work according to the same physical principle or according to different principles.

In some embodiments of the present invention the runtime of a fluid which is conveyed by means of a blood pump trough or in an extracorporeal blood circuit (which may be in some embodiments e.g. dialysis fluid or substitute fluid or blood) is measured, detected, determined or calculated. In these embodiments the method of the present invention comprises conveying of a fluid through the extracorporeal blood circuit or parts thereof by means of a pump, e.g. a blood pump. The pump conveys with a predetermined constant flow or with a non-constant but in another way predetermined flow which allows measuring, detecting, determining or calculating the conveyed fluid volume during an overseen period of time. Such a predetermined flow may be a continuously increasing flow or a flow which is increased stepwisely by a known step size at predetermined points of time.

In these embodiments the point of time when the fluid appears at a first sensor of the extracorporeal blood circuit is identified. This point of time is denoted as a first point of time.

In these embodiments the point of time when the fluid appears at a second sensor of the extracorporeal blood circuit is identified. This point of time is denoted as a second point of time.

In these embodiments the time difference between the first point of time and the second point of time is determined or calculated.

In these embodiments the detecting, determining or calculating of the size of the volume of the introduced fluid comprises multiplying the time difference with the constant flow of the blood pump or consists of such a multiplication.

In these embodiments the volume of the extracorporeal blood circuit may by determined or detected by means of the run time of the fluid, e.g. of the blood, from the first to the second sensor, if the flow rate of the pump used, e.g. a blood pump, is known. The flow rate of the pump may be a result of a constant or otherwise known flow rate between the first and the second point of time.

This way, the total volume of the conveyed fluid and therefore the joint filling volume of the tubing sections and of the treatment device (e.g. a dialyzer) may be determined by the time difference or the run time and the pump rate, pump power or pump output per time.

When the filling volume of the extracorporeal blood circuit, especially of its tubing sections, is known, the type of the treatment device (e.g. the dialyzer) may be determined, since each type of treatment device accommodates a particular volume.

Each of the mentioned optical sensors may be an optical venous blood detector (for detecting blood in the venous line of the extracorporeal blood circuit), an optical sensor for measuring or determining at least one blood parameter, or any other type of sensor. A blood parameter may be for example the relative blood volume, the concentration of haemoglobin or the hematocrit. Other optical detectors which may be used during the method according to the present invention are not adapted for measuring blood parameters.

A sensor for measuring or determining at least one blood parameter as described above is in some embodiments of the present invention a device for blood measurements, as it is disclosed in the European Patent Application No. EP 1 748 292 A1 and/or International Patent Publication NO. WO 2004/057313 A1. The respective disclosures of both patent applications, and especially the wording of the claims as noted therein, are hereby incorporated in their entirety by reference thereto.

An optical sensor for measuring or determining at least one blood parameter may especially be a device which comprises a measuring unit or device having a light emitter and a light detector. Using same, light with a predetermined wave length is induced into a section of the extracorporeal blood circuit, e.g. an arterial section. The section is opaque or translucent, especially for infrared light. By the optical sensor for measuring at least one blood parameter a fluid, e.g. blood, may be detected, for example by means of the ratio or relation between the intensity of the entering light and the intensity of the exiting light.

In some embodiments according to the present invention, the optical sensor for measuring at least one blood parameter is embodied to measure more blood parameters, e.g. the relative blood volume, the concentration of haemoglobin and/or the hematocrit. The control device or regulating device is configured accordingly.

If the presence of fluid is detected by light, in some embodiments according to the present invention the use of light with a wavelength between 790 and 820 nm, preferably between 800 and 810 nm, and especially preferably of 805 nm, is provided.

If the presence or appearance of a fluid shall be detected or determined by light, in certain embodiments according to the present invention the light emitter and the light detector are arranged at a section of the extracorporeal blood circuit for measuring in this section or through it which is placed between the arterial patient needle and blood pump.

This section is in some embodiments according to the present invention stiffer or more stably guided or housed than at least one other section of the extracorporeal blood circuit, as compared to a section downstream of the blood pump, or any or all other sections of the extracorporeal blood circuit.

The stiffer section is in certain embodiments according to the present invention a section, which is at least partially surrounded or enclosed at its exterior or its circumference by a limiting element or a sleeve (hereafter: sleeve). The sleeve applies or exerts pressure in certain embodiments according to the present invention to the section which it surrounds, for example such that the section has another cross-section profile as compared to in front of and/or beyond the sleeve. That is why it is called stiff(er). This can advantageously improve measurement accuracy by the light detector.

By way of example, the round or circular cross-section of the blood tube or tubing may be formed or shaped into a rectangular or angular cross-section or a cross section with at least one or two straight sides. An example of such a sleeve or of the underlying idea is disclosed in the above mentioned European Patent Application No. EP 1 748 292 A1 and International Patent Publication No. WO 2004/057313 A1, for example in FIGS. 1 to 5 therein. The respective disclosures of both patent applications are hereby completely incorporated in their entirety by reference thereto.

The compression of the blood tube or tubing by means of the sleeve can especially cause a predetermined pressure and/or a predetermined change of the shape or the cross section of the blood tube. The blood tubing section can therefore be pressed in a defined way.

The sleeve can be especially embodied as an elongated container or box in some embodiments according to the present invention.

The sleeve can be especially embodied with mountings or passages for the light emitter and/or the light detector in certain embodiments according to the present invention.

The first sensor as well as the second sensor may independently of each other be sensors which determine the presence of a fluid by means of optical density, ultrasound, acoustic or temperature measurements.

In some embodiments according to the present invention the measured or determined time difference is used for controlling the process of the blood treatment or for dismantling the blood treatment device after the treatment has come to an end. The knowledge of the time difference can, for example, be used for an automatic stop of the reinfusion of the blood after the end of the treatment.

In certain embodiments of the present invention, the recognition device is provided for recognizing a fluid-air limit. It can thus indicate when or if the air present in the (still unused) extracorporeal blood circuit is displaced upstream from the recognition device by the filled-in fluid and removed from the extracorporeal blood circuit, e.g., via a ventilation device.

In certain embodiments of the present invention, the volume of the fluid is detected via the (number of) rotor turns of a conveying device by means of which the extracorporeal blood circuit was filled.

The conveying device may be a tube roller pump, for example a tube roller pump which in treatment methods is used for conveying blood (blood pump) and/or substituate (substituate pump) and/or dialysate.

In further embodiments of the present invention, the volume of the fluid is detected via the weight reduction of a source of the fluid, e.g., a bag of liquid. The weight reduction may be detected, for example, by weighing the bag of liquid.

In certain embodiments of the present invention, the method according to the present invention encompasses comparing the determined parameter with (detected and stored) parameters of a multitude of usable medical functional devices for identifying or allocating the extracorporeal blood circuit to a medical functional device or component which is present or used herein. Such comparing corresponds to or encompasses in some embodiments according to the present invention processing as discussed above.

Comparing may take place, e.g., by means of a comparative table.

In further embodiments, the method according to the present invention encompasses comparing the determined parameter with (detected and stored) parameters of a multitude of usable treatment devices for identifying a utilized treatment device.

The multitude of the possible and/or useable medical functional devices or of the possible and/or useable treatment devices or information regarding each of those may be stored in suitable or adapted tables.

A preparation which usually takes place before use of the extracorporeal blood circuit for a treatment, for example by priming and/or flushing serves, as mentioned above, to remove possibly present production residues (due to the production of the treatment device and/or of the blood tube set) and/or air from the blood circuit or the components connected herewith. The fluid amount or the fluid volume required for flushing or priming is usually higher than the fluid amount or the filling or fluid volume required for simple filling of the extracorporeal blood circuit. In the state of the art, a generally applicable minimum volume of, e.g., 500 ml is defined for priming/flushing. This definition is obviously not aligned, adapted or even optimized to each concretely used extracorporeal blood tube set and its components, for example the utilized blood filter.

The method according to the present invention encompasses in certain embodiments defining a minimum, ideal and/or maximum priming or flush volume for priming or flushing the extracorporeal blood circuit by means of the determined parameter. Thus, the priming or flush volume is advantageously adjusted to the actually used extracorporeal blood circuit and its components by means of the determined parameter. Hereby, the parameter may for example be the filling volume of the blood circuit, or its type.

In certain embodiments, a minimum flush volume $V\_min$ for preparing the later occurring treatment method which is not subject or part of the present invention may follow, e.g., the following mathematical function:

$$V\_min = a*V\_Set + b*V\_Dial$$

Hereby, $V\_min$ is the minimum flush volume when preparing the treatment method; $V\_Set$ is the volume of the medical functional device, in particular of a blood tube set; $V\_Dial$ is the volume of the treatment device, in particular of a dialyzer or blood filter; and $a$ and $b$ are each numbers or constants.

In certain embodiments, $a$ is an arbitrary number which may assume values of, in particular, 1 to 3.

In certain embodiments, $b$ is an arbitrary number which may assume values of, in particular, 2 to 5.

In some embodiments, further factors such as (treatment) instructions or the like may have influence on the determination of the priming or flush volume.

In certain embodiments according to the present invention, the method encompasses defining or influencing a control of the (later) treatment method taking into account or depending on the determined parameter.

In some embodiments, the method according to the present invention encompasses defining maximum and/or minimum pump rates, (automatic) defining of reinfusion volumes or the like taking into account or depending on the determined parameter.

In certain embodiments, reinfusion volumes are such volumes of a liquid (e.g., substitute, dialyzing liquid or flushing liquid) which are necessary for flushing out the blood still contained in the extracorporeal blood circuit at the end of the blood treatment, with the aim of returning the blood to the patient.

In certain embodiments, the method according to the present invention encompasses blocking treatment modalities and/or restricting treatment parameters of the (later) treatment method, taking into account or depending on the determined parameter.

Some or all embodiments according to the present invention may comprise one or more advantages named above or hereafter.

The present invention advantageously provides a simple and little elaborate method for (further) automation of a treatment method.

The present invention is advantageously usable for all treatment apparatuses with extracorporeal blood circuits.

By means of the method according to the present invention, it is, based on the information of the (filling) volume which was gained during initial filling of an extracorporeal blood circuit or a different parameter such as the type of the utilized blood circuit or the like, in some embodiments advantageously possible to make an individualized specification of the liquid volume which is to be recirculated during subsequent flushing. This may contribute to an ideal flushing effect, a minimum flushing effect and/or to an economical use of flushing fluid.

By means of the method according to the present invention, it is, based on the information of the (filling) volume which was gained during initial filling of an extracorporeal blood circuit, in some embodiments advantageously possible to admit or block certain treatment modalities, corresponding to the recognized suitability, size, or the type of extracorporeal blood circuit and/or utilized treatment apparatus. This may advantageously contribute to the further automation of the preparation of a treatment and/or the treatment procedure itself. Herewith, furthermore the safety of the system as well as patients' safety may be increased.

The present invention is advantageously especially easy to implement as it oftentimes encompasses only upgrading on the side of the software of already operated treatment apparatuses.

Such upgrading or retrofitting may take place, e.g., by implementing the source code or machine code of the operating software in the control device of a treatment apparatus.

Hereafter, the present invention is exemplarily described with reference to the appended figures in which identical reference numerals identify identical or similar elements.

DETAILED DESCRIPTION

Figure 1:
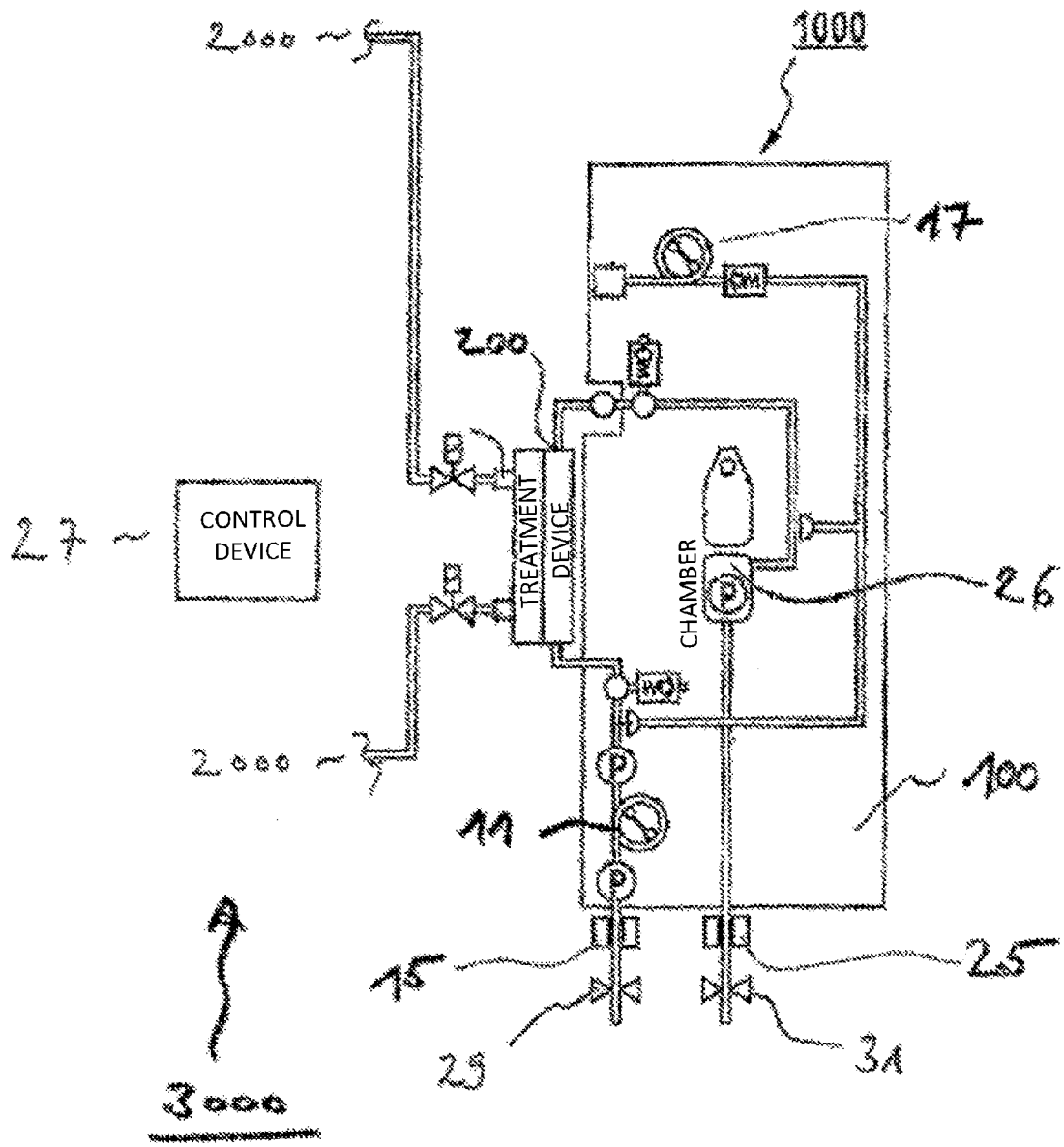
FIG. 1 shows a schematic illustration of an extracorporeal blood circuit which may be prepared for its use by means of the method according to the present invention, as well as of a dialysate circuit.

FIG. 1 schematically shows an extracorporeal blood circuit 1000 as well as, in outlines, a dialysate circuit 2000 of a treatment apparatus 3000, for example a hemodiafiltration machine.

The extracorporeal blood circuit 1000 comprises, is connected to or at least in sections integrated into a medical functional device 100, for example a (disposable) blood cassette.

The functional device 100 is functionally coupled to the treatment apparatus 3000 and functionally interacts with the pump drives, actors and sensors of the treatment apparatus 3000 which is only outlined in FIG. 1. The pump drives, actors and sensors of the treatment apparatus 3000 functionally interact with a control and/or regulating device 27 of the treatment apparatus 3000. They may be in signal connection with the control and/or regulating device.

The extracorporeal blood circuit 1000 is connected to a treatment device 200, for example a dialyzer or a blood filter.

In or at the extracorporeal blood circuit 1000, a blood pump 11 as well as a substitute pump 17 are arranged. The blood pump 11 and the substitute pump 17 may convey blood or substituate in a later occurring treatment method.

The blood pump 11 and/or the substitute pump 17 may be utilized in the sense of the method according to the present invention as conveying device(s) for conveying the fluid to fill the extracorporeal blood circuit 1000. The same applies to a pump of the dialysate circuit; the pump is not illustrated in FIG. 1.

The extracorporeal blood circuit 1000 comprises an arterial air bubble detector 15 ("art. ABD"). It further comprises a venous air bubble detector 25 ("ven. ABD"). For example, the venous air bubble detector 25 may be utilized in the extracorporeal blood circuit 1000 as a recognition device for recognizing a filling state.

The method according to the present invention serves in some embodiments according to the present invention to determine the fluid volume through the treatment apparatus 3000, the filling volume being required for filling the extracorporeal blood circuit 1000, i.e. the blood side of the line system.

In certain embodiments of the method according to the present invention, the volume of the fluid, which was introduced for filling the extracorporeal blood circuit 1000, is detected which is required for triggering a level detection (for example, at a venous chamber 26) or a message by the venous air bubble detector 25. The detected volume may be defined, e.g., by determining the required rotor turns of the blood pump 11 and/or of the substitute pump 17, or by weighing a liquid bag with fresh flushing/substituate solution. The detected volume may be multiplied with a factor in order to specify or adjust the required flush volume.

If the liquid level drops again at the detection point, i.e. at the detection position or at the recognition device, during filling, for example because remaining air dissolves out of the treatment device 200, the volume required for raising the level again may be added to the already detected volume. The further use of the such determined cumulative volume may hereby advantageously increase the accuracy of determining the of the detected volume.

The detected volume is in certain embodiments used for identifying a utilized blood tube set. Identifying the blood tube set may for example take place by means of a comparative table in which typical filling volumes for different disposable configurations or blood tube/blood filter combinations are recorded.

The comparative table is in some embodiments according to the present invention saved within the control and/or regulating device 27 in a data storage or may be saved in it according to the present invention.

The control and/or regulating device 27 comprises in some embodiments according to the present invention a device for evaluating measurement data and calculating a filling volume, in particular the cumulative filling volume from the measurement data. It may additionally comprise a device for comparing the calculated filling volume with the data from the comparative table, further a device for allocating the calculated filling volume to certain predefined blood tube sets from the comparative table. The above-mentioned devices may be combined in one single device.

Thus, for example different blood tube systems for, e.g., pediatric dialysis and dialysis for adults, or different treatment methods (single-needle/double-needle) may be advantageously easily distinguished. Depending on the identified type of disposable, treatment modalities may be blocked and/or treatment parameters may be restricted at the treatment apparatus, in particular automatically and without the involvement of the supervisor.

In further embodiments, the detected volume is used for identifying the utilized treatment device 200, for example a utilized dialyzer.

For refinement of the identification, further (supplemental) characteristic features which are available to the treatment apparatus can be taken into account (for example, a filling volume on the dialysate side, flow resistances on the blood and/or dialysate side, the transmembrane pressure and the like).

Further, FIG. 1 shows an arterial blood tube clamp 29 and a venous blood tube clamp 31.

Figure 2:
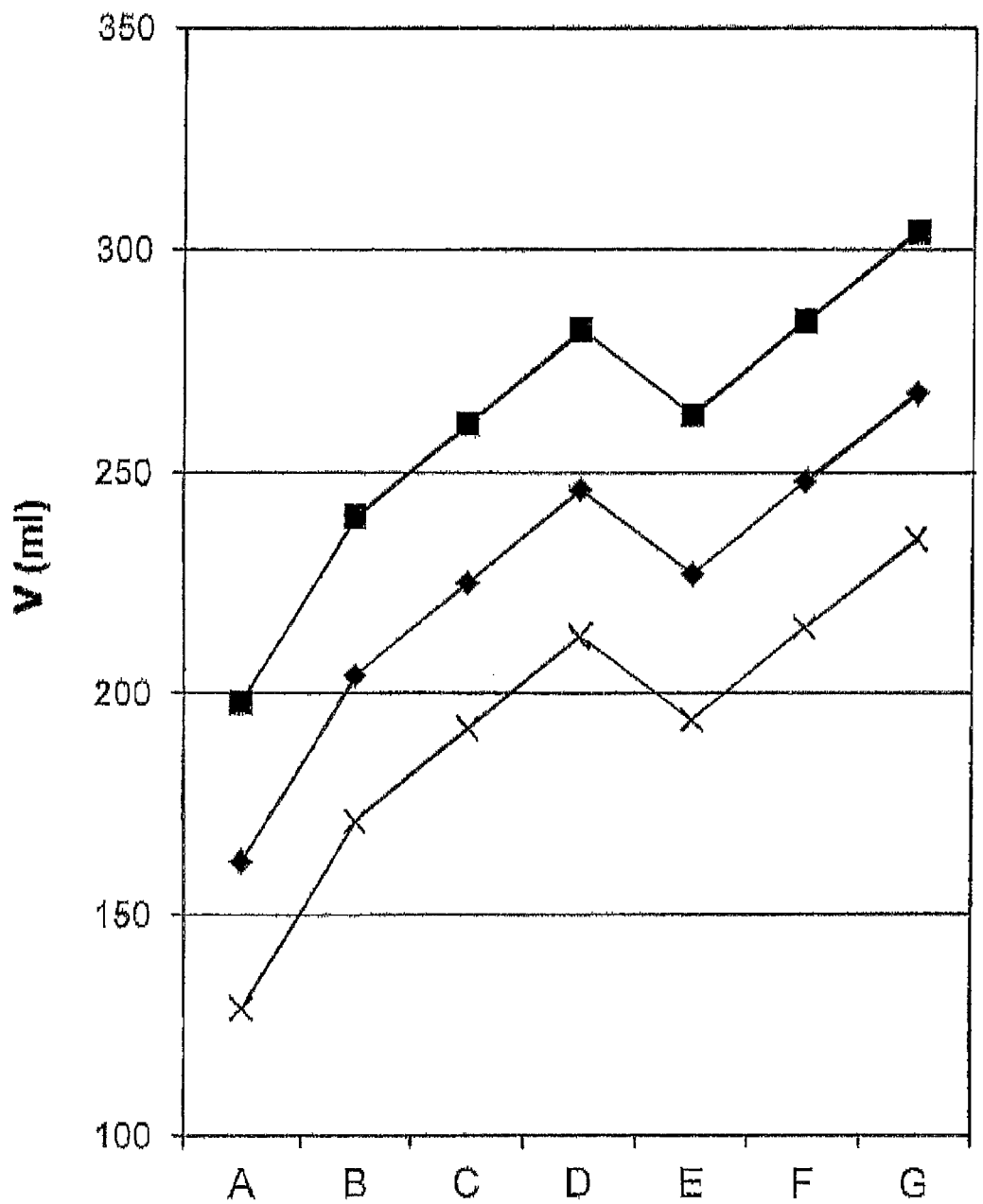
FIG. 2 illustrates the filling volume of different dialyzers and their identifiability by means of the method according to the present invention.

FIG. 2 shows different filling volumes V (in ml) of a first extracorporeal blood circuit for a single-needle treatment (associated values are marked with squares), of a second extracorporeal blood circuit for a double-needle treatment (associated values are marked with rhombi), and of a third extracorporeal blood circuit for a blood cassette (associated values are marked with crosses).

The filling volume of the first blood circuit (squares) is 166 ml. The filling volume of the second blood circuit (rhombi) is 130 ml. The filling volume of the third blood circuit (crosses) is 97 ml. These specifications each apply to the blood circuit as long as it is not connected with a blood filter.

FIG. 2 shows how the whole filling volume of the above-named blood circuits increases, and increases in different ways, as soon as they are connected with one of the filters A, B, C, D, E, F or G.

It is therefore well recognizable from FIG. 2 that knowledge of the filling volume of a concrete blood circuit already exhibits with which filter it is connected at the moment of its filling in the sense of the present invention.

In certain embodiments of the method according to the present invention, the method encompasses defining parameters or parameter values for the method control in the subsequent treatment, e.g., defining maximum/minimum admissible pump rates (small dialyzers have smaller recommended blood flows than larger ones), automatically defining reinfusion volumes, or the like.

Table 1, which reflects this, is hereafter shown for the minimum flow min_Flow and the maximum flow max_Flow for the blood filters A to G as mentioned above, which have different filling volumes or blood volumes.

TABLE 1

| blood filter | blood volume | min_Flow | max_Flow |
|---|---|---|---|
| A | 32 | 50 | 200 |
| B | 74 | 150 | 400 |
| C | 95 | 200 | 500 |
| D | 116 | 250 | 600 |
| E | 97 | 150 | 400 |
| F | 118 | 200 | 500 |
| G | 138 | 300 | 600 |

It is thus recognizable for the person skilled in the art that the knowledge of the utilized filter type, which may be determined by means of the method according to the present invention, can also be used for controlling the treatment apparatus during a subsequent treatment. Thus, a minimum or maximum flow (rate) (min_Flow or max_Flow), which depends on the type of blood filter, can automatically be adjusted.

Figure 3:
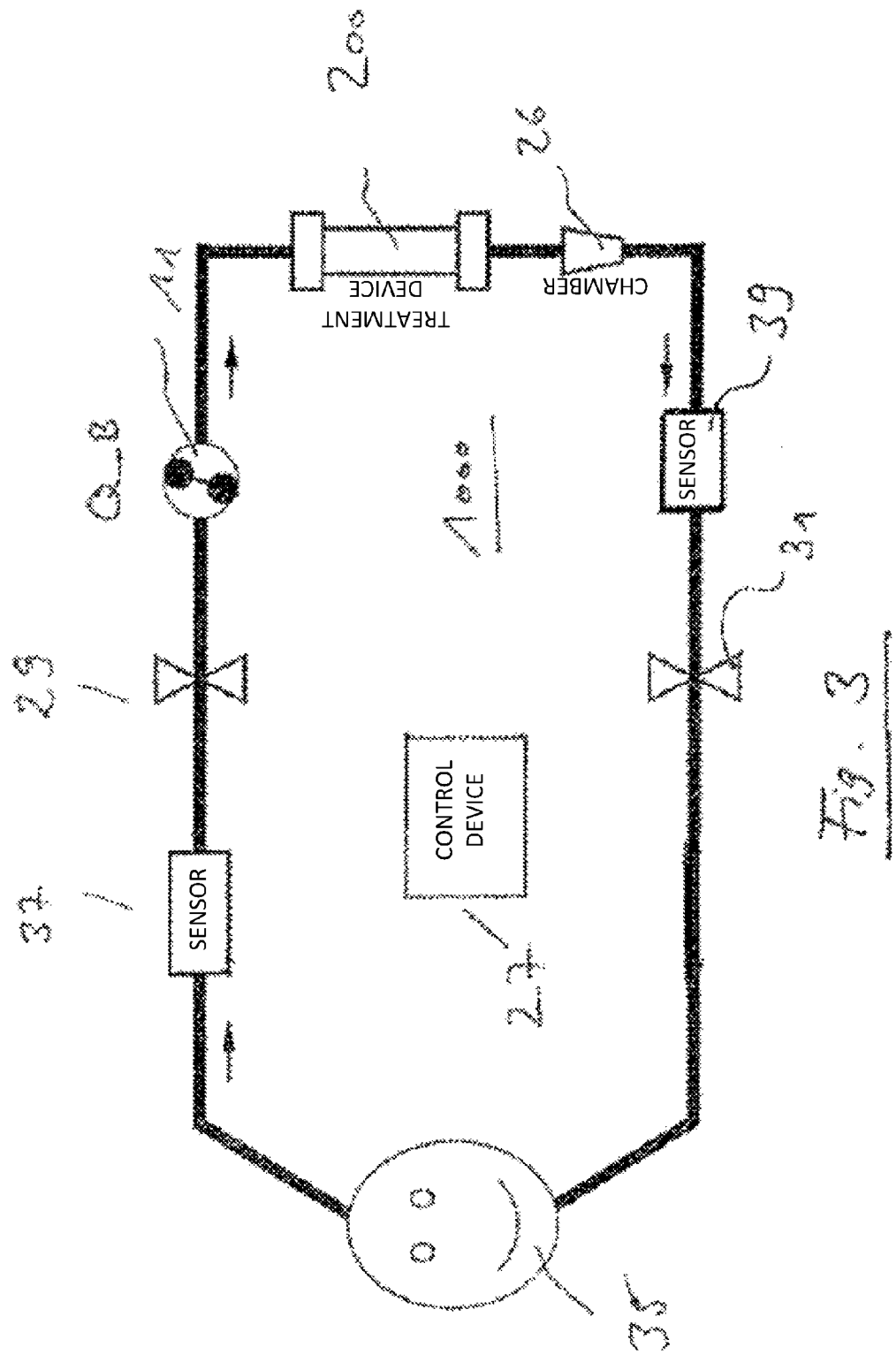
FIG. 3 shows a schematic illustration of yet another extracorporeal blood circuit, which can be prepared for its use or for a concluding rinsing by means of the method according to the present invention.

FIG. 3 shows a schematic illustration of yet another extracorporeal blood circuit 1000. The method according to the present invention can be executed in the following way, by means of example. Hereby it is assumed, that the blood treatment device 200 is a dialyzer.

When a very schematically illustrated patient 35 has been connected to an extracorporeal blood circuit, blood pump 11 is started with a constant blood flow Q_B (ml/min). The blood passes a first sensor 37 and the arterial blood tube clamp 29 and into the extracorporeal blood circuit.

The entering blood is thereby recognized by a first sensor 37 (e.g. an optical sensor or an optical sensor for measuring at least one blood parameter) at a first point of time t1 (sec).

At a second point of time t2 (sec), the blood is recognized in the venous line by a second sensor 39, e.g. an optical sensor, once it has arrived there. The detection of blood by means of the second sensor may for example take place by infrared transmission measurement.

In some embodiments according to the present invention the second sensor 39 may be coupled with an air bubble detection device or may be provided therewith in one common assembly. The second sensor 39 is in certain embodiments arranged upstream of the venous blood tube clamp 31. In some embodiments according to the present invention it is arranged downstream of the venous chamber 26 or the venous bubble chamber.

The volume V_Set of the entire extracorporeal blood circuit 1000 can be calculated from the constant blood flow Q_B (ml/min) and the time difference between the first point of time t1 (sec) and the second point of time t2 (sec) as follows:

$$V\_Set = (t2 - t1) \times Q\_B / 60 \text{ (in ml)} \quad (1)$$

Due to the known relation:

$$V\_Set = V\_Dial + V\_Schlauch \quad (2)$$

with V_Set being the volume of the entire blood tube set, the Volume V_Dial of the Dialyzer can be measured, if the volume of the tube V_Schlauch is known, by way of:

$$V\_Dial = V\_Set - V\_Schlauch. \quad (3)$$

Components which are shown in the extracorporeal blood circuit of FIG. 1 may be part of the extracorporeal blood circuit of FIG. 3, and vice versa.

What is claimed is:

1. A method for determining at least one parameter of an extracorporeal blood circuit, the method comprising:
   introducing a medical liquid at a flow rate into the extracorporeal blood circuit, the extracorporeal blood circuit comprising a blood treatment device to which a dialysate circuit is connected;
   detecting, at a first point in time, the introduced medical liquid at a first sensor location along the extracorporeal blood circuit;
   detecting, at a second point in time, the introduced medical liquid at a second sensor location along the extracorporeal blood circuit;
   determining or calculating a volume of the introduced medical liquid based on the flow rate and based on a time difference between the first point in time and the second point in time; and
   determining the at least one parameter of the extracorporeal blood circuit, wherein the at least one parameter of the extracorporeal blood circuit is determined based on the volume of the introduced medical liquid.

2. The method according to claim 1, wherein the introducing occurs at least one of prior to a treatment using the extracorporeal blood circuit and prior to a flushing process.

3. The method according to claim 1, further comprising:
   storing a value of the determined or calculated volume of the introduced medical liquid for maintaining the at least one parameter of the extracorporeal blood circuit.

4. The method according to claim 1, wherein the volume of the introduced medical liquid is a cumulative volume.

5. The method according to claim 1, further comprising:
   conveying the fluid through the at least one of the extracorporeal blood circuit and the predetermined section thereof by a blood pump having at least one of a constant and a predetermined flow;
   determining a point in time when the fluid appears at a first sensor of the extracorporeal blood circuit as a first point in time;
   determining a point in time when the fluid appears at a second sensor of the extracorporeal blood circuit as a second point in time;
   determining a time difference between the first point in time and the second point in time;
   wherein the one of detecting, determining and calculating of the size of the volume of the introduced fluid comprises multiplying the time difference with the constant flow of the blood pump.

6. The method according to claim 5, wherein at least one of the first sensor and the second sensor are optical sensors.

7. The method according to claim 5, wherein at least one of the first sensor and the second sensor are sensors for detecting the fluid by one of ultrasound, acoustic and temperature measurements.

8. The method according to claim 1, wherein the detecting takes place by a detection device which comprises or is connected to at least one recognition device for recognizing a fluid or a fluid condition;
   wherein the recognition device is chosen from a group consisting of a level detector, an air detector, an optical detector, an ultrasound detector, a sound detector and combinations thereof.

9. The method according to claim 1, wherein a value of the volume of the introduced medical liquid is detected by rotor turns of a conveying device for conveying the medical liquid.

10. The method according to claim 1, wherein the volume of the introduced medical liquid is detected by a weight reduction of a source of the medical liquid.

11. The method according to claim 1, further comprising:
    comparing the determined at least one parameter of the extracorporeal blood circuit with parameters of a multitude of utilizable medical functional devices to identify a utilized medical functional device.

12. The method according to claim 1, further comprising:
    comparing the determined at least one parameter of the extracorporeal blood circuit with parameters of a multitude of utilizable blood treatment devices to identify a utilized blood treatment device.

13. The method according to claim 1, further comprising:
    defining at least one of: (a) a minimum priming or flush volume and (b) a maximum priming or flush volume of the extracorporeal blood circuit based on the determined at least one parameter of the extracorporeal blood circuit.

14. The method according to claim 13, wherein the minimum flush volume for flushing the extracorporeal blood circuit for preparation of a treatment method is defined by the following mathematical function:

$$V\_min = a * V\_Set + b * V\_Dial$$

where V_min is the minimum flush volume when preparing the treatment method;
V_Set is a volume of a medical functional device;
V_Dial is a volume of a blood treatment device; and
a and b are constants.

15. The method according to claim 14, wherein a is a number in a range from 1 to 3.

16. The method according to claim 14, wherein b is a number in a range from 2 to 5.

17. The method according to claim 1, further comprising:
    defining or controlling flow rates of a treatment method based on the determined at least one parameter of the extracorporeal blood circuit.

18. The method according to claim 1, further comprising:
    at least one of: (i) blocking treatment modalities and (ii) restricting treatment parameters of a treatment method when using the extracorporeal blood circuit based on the determined at least one parameter of the extracorporeal blood circuit.

19. The method according to claim 1, wherein the extracorporeal blood circuit is or comprises at least one of a medical functional device and a blood tube set.

20. A non-transitory computer readable storage medium with an executable program stored thereon, wherein the program instructs a programmable computer system so as to execute the steps of the method according to claim 1.

21. The medium according to claim 20, wherein the medium is a disk, CD, DVD or EPROM.

22. A computer program product with an executable program code stored on a non-transitory computer readable medium, wherein the program code instructs a programmable computer system so as to execute the steps of the method according to claim 1.

23. A control device of a medical treatment apparatus, the control device configured to:
    initiate a conveyance at a flow rate of a volume of a medical liquid into an extracorporeal blood circuit of the medical treatment apparatus, the extracorporeal blood circuit comprising a blood treatment device to which a dialysate circuit is connected;

determine a first point in time when the medical liquid is detected at a first sensor location along the extracorporeal blood circuit;

determine a second point in time when the medical liquid is detected at a second sensor location along the extracorporeal blood circuit;

determine the volume of the medical liquid conveyed into the extracorporeal blood circuit based on the flow rate and based on a time difference between the first point in time and the second point in time; and determine at least one parameter of the extracorporeal blood circuit based on the determined volume of the medical liquid conveyed into the extracorporeal blood circuit.

24. A medical treatment apparatus comprising a control device and an extracorporeal blood circuit, the apparatus configured to:

convey at a flow rate a volume of a medical liquid into the extracorporeal blood circuit, the extracorporeal blood circuit comprising a blood treatment device to which a dialysate circuit is connected;

determine, by the control device, a first point in time when the medical liquid is detected at a first sensor located along the extracorporeal blood circuit;

determine, by the control device, a second point in time when the medical liquid is detected at a second sensor located along the extracorporeal blood circuit;

determine, by the control device, the volume of the medical liquid conveyed into the extracorporeal blood circuit based on the flow rate and based on a time difference between the first point in time and the second point in time; and determine, by the control device, at least one parameter of the extracorporeal blood circuit based on the determined volume of the medical liquid conveyed into the extracorporeal blood circuit.

25. The medical treatment apparatus according to claim 24, wherein the apparatus is at least one of a blood treatment apparatus, dialysis apparatus, hemodialysis apparatus, hemofiltration apparatus, and hemodiafiltration apparatus.

26. The medical treatment apparatus according to claim 24, further comprising:

a control device configured for executing a method comprising:

filing the extracorporeal blood circuit by introducing the medical liquid; and detecting, determining or calculating the volume of the introduced medical liquid.

* * * * *